United States Patent [19]

Ouvrard

[11] 3,945,243

[45] Mar. 23, 1976

[54] METHOD AND DEVICE FOR THE CONTINUOUS AUTOMATIC ANALYSIS OF THE FILTERABILITY POINT OF LIQUID SUBSTANCES, PARTICULARLY DIESEL OIL

[75] Inventor: Paul Ouvrard, Saint-Nazaire, France

[73] Assignee: Societe Anonyme dite: Antar Petroles de l'Atlantique, Paris, France

[22] Filed: Sept. 13, 1974

[21] Appl. No.: 505,645

[30] Foreign Application Priority Data
Sept. 19, 1973 France ............................ 73.33670

[52] U.S. Cl. ................................. 73/17 R; 73/61.4
[51] Int. Cl.² ........................................ G01N 25/02
[58] Field of Search ........................... 73/17 R, 61.4

[56] References Cited
UNITED STATES PATENTS

| | | | |
|---|---|---|---|
| 2,591,084 | 4/1952 | Martin | 73/17 R |
| 2,750,433 | 6/1956 | Tourneau et al. | 73/17 R X |
| 2,997,874 | 8/1961 | Billuris et al. | 73/17 R X |
| 3,143,876 | 8/1964 | Wallgren | 73/17 R |
| 3,213,668 | 10/1965 | Thompson | 73/17 R |
| 3,577,765 | 5/1971 | Bertoglio et al. | 73/17 R |
| 3,872,710 | 3/1975 | Louvel | 73/17 R |

*Primary Examiner*—Richard C. Queisser
*Assistant Examiner*—Joseph W. Roskos
*Attorney, Agent, or Firm*—Hammond & Littell

[57] ABSTRACT

A method and apparatus for the continuous automatic analysis of the filterability point of liquid substances such as Diesel oil. The Diesel oil flows through a measuring circuit at a constant flow rate by means of a volumetric pump. The temperature in the measuring circuit is maintained sufficiently below the assumed filterability point of the substance. A heating element is provided along the flow path of the Diesel oil for melting microcrystals which form on the filter in the filtering chamber of the measuring circuit, or alternatively, in a tube of the measuring circuit. A differential pressure responsive device with a switch is connected between the inlet and outlet of the measuring circuit for detecting the pressure drop across the circuit. The switch of the device is actuated in response to the pressure drop falling below a predetermined level which is caused by a build-up of micro-crystals, for turning on the heating element and melting the microcrystals. The heating element is then automatically turned off when all the micro-crystals have melted by the corresponding increase in pressure drop across the measuring circuit in response to which the device actuates the switch once again back to its initial position.

4 Claims, 8 Drawing Figures

FIG.7

METHOD AND DEVICE FOR THE CONTINUOUS AUTOMATIC ANALYSIS OF THE FILTERABILITY POINT OF LIQUID SUBSTANCES, PARTICULARLY DIESEL OIL

The present invention relates to a method and device for the continuous automatic analysis of the "filterability point" of liquid substances, particularly Diesel oil in the process of manufacture.

In the present description the term filterability point generally defines the flowability of a liquid substance as its temperature drops.

Diesel oil intended for use in Diesel engines must pass a particular test, called the filterability point test. The filterability point is the point at which the filters are clogged. The test carried out on Diesel oil is therefore intended to determine the value of the temperature below which the appearance of microcrystals of paraffin in the midst of the liquid is capable of blocking or clogging the filters protecting the injectors.

Up to now this analysis has been carried out in the laboratory with the aid of equipment whose modus operandi will be given in brief hereinafter with reference to FIG. 1 of the accompanying drawings.

The substance 1 to be analyzed contained in the measuring test-tube 2 is immersed in a cooling bath 3 whose temperature is maintained at a value sufficiently below the assumed filterability point.

The substance 1 passes into a tube 4 connected to a chamber 5 and is filtered by a filter 6 having a standardized mesh and positioned inside the chamber 5.

Periodically a partial vacuum of constant magnitude is applied to the upper part of the chamber 5 until 20 cubic centimeters of liquid has passed through the filter. The manometer 10 monitors the value of the partial vacuum applied. A graduation 8 located along the suction tube enables accurate measurement of volumetric displacement.

By means of the two-way valve 9 located downstream of the filtering chamber 5 during suction, when the substance 1 reaches the graduation 8 corresponding to a quantity of 20 cubic centimeters of liquid, the partial vacuum is then cut off by bringing the downstream end of the filtering chamber into communication with ambient air, thereby enabling the return of the substance displaced back into the test-tube 2.

In the filtering chamber 5, downstream of the filter itself, a device 7 for measuring the temperature is positioned, the principle of measurement consists in marking the temperature of the filering Diesel oil above which the displacement of 20 cubic centimeters requires more than one minute.

In the analysis procedure, the energy for filtration (in this case the value of the partial vacuum drawing up the liquid) is constant and the flow rate is variable. In fact the displacement time for 20 cubic centimeters of liquid 1 is a few seconds so long as the Diesel oil is at a temperature sufficiently higher than the filterability point, however, this time increases rapidly as temperature aproaches the filterability point since the clogging of the filter reduces the effective section of passage therethrough.

The equipment is controlled manually by an operator; there are also automated setups in which the successive sequences of suction and measurement of displacement time are controlled automatically.

However, these techniques which are very useful in the laboratory cannot be used on production sites for continuous quality control, at all times.

The method and apparatus according to the present invention have been conceived precisely to provide continuous automatic control.

Generally speaking, in the method according to the invention, the flow rate of the substance to be analyzed is maintained constant while variations in the pressure drop are measured as the temperature of the circulating substance drops.

preferably, the method for the continuous automatic analysis of the filterability point of liquid substances, particularly Diesel oil, comprises passing a substance to be analyzed through a measuring circuit at a constant flow rate, the temperature therein being maintained at a value sufficiently below the assumed filterability point of the substance, heating means being provided along the flow path of the liquid substance in said circuit, automatically turning on and off said heating means at two characteristic temperatures, detected by measuring the pressure drop of the substance at the inlet and outlet of said circuit, variations of the pressure drop being determined as a function of the temperature, the values of the pressure drop thus measured being utilized as control data for turning on and off the heating means, when the outlet temperature reaches one of the two characteristic temperatures, the first characteristic temperature corresponding to a temperature slightly below than the filterability point, the other characteristic temperature corresponding to a temperature sufficiently above the filterability point, and continuously recording the temperature of the substance being continuously recorded at the outlet of the circuit, this temperature constituting a representative value of the filterability point of the substance.

The increase of the pressure drop brings about the closing of pressure responsive switching means which controls power supplied to the heating means.

The hysteresis of the pressure responsive switching means is controlled so that the heating stops as soon as the value $\Delta P$ (pressure drop) drops to a value slightly above the initial value.

An apparatus for carrying out said method generally comprises means to have the substance to be analysed flowing at a constant rate along a path including measuring means in said path, of flowing substance, said measuring means having an inlet and an outlet end means to maintain the temperature of said measuring means at a value sufficiently below the assumed point of filterability of said substance, heating means provided along the said circuit measuring means, means to pick up the values of the difference of pressures between said respective inlet and outlet of the measuring means said difference being a function of the temperature, switching means responsive to said differential values of pressures for respectively turning automatically on and off the heating means when the temperature of the substance at said outlet reaches the one of two characteristic temperatures which correspond respectively slightly below and sufficiently above the point of filterability, means to continuously record the values of the temperature of the substance at said outlet end, whereby said outlet temperatures are representative of the filterability point.

Specifically an apparatus for carrying out the method according to the invention may comprise a geared volumetric pump connected at its suction side to a source of the liquid substance to be analyzed and at its delivery side to the measuring chamber which is located at the lower portion of an insulated housing containing a cooling bath, the housing being provided with cooling means and temperature measuring means which is readable from outside the housing, the measuring chamber includes a filtering chamber in which a filter with standardized mesh is provided, a thermosensitive element being disposed at the outlet or downstream side of the filter along the flow path of the liquid substance and associated with a recording device, heating means being disposed in the lower portion of the measuring chamber, the said means being connected outside the housing to two leads, one of the leads being directly connected to a power supply and the other lead being connected to the switch of a differential pressure responsive switching means connected between the inlet of the measuring chamber, i.e., at the outlet of the volumetric pump and the outlet of the measuring chamber, downstream of the filter.

Alternatively, the apparatus for carrying out the method according to the invention comprises at the inlet means for pumping Diesel oil to be analyzed and at the delivery side a measuring chamber is connected to the inlet by a measuring circuit tube in which a heating element is provided extending along the entire length of the tube and into the upstream end of the measuring chamber, the measuring chamber being located in an insulated housing and including a filtering chamber in which a filter is located, a thermosensitive element being disposed at the downstream side of the filter along the flow path of the liquid substance and the high pressure side of a differential pressure responsive switching means connected at the inlet of the measuring circuit tube and the low pressure side the outlet of the measuring chamber after flowing by the thermosensitive element.

A preferred embodiment of an apparatus for carrying out the method according to the invention comprises a measuring circuit including a capillary tube of stainless steel through which the liquid substance to be analyzed flows, the flow rate therein being maintained constant by a small volumetric pump, the capillary tube being immersed along a large portion of its length in a cooling bath contained in a measuring well, the inlet and outlet ends of the capillary tube in the well being electrically connected outside the well to two leads, one of the leads being connected directly to the power supply and the other being connected to a switch associated with differential pressure responsive switching means which is operatively connected between the inlet and outlet of the capillary tube, the thermosensitive element being disposed at the outlet of the measuring well along the flow path of the substance to be analyzed and associated with a recording device.

According to preferred complementary features of the above apparatus:

the thermosensitive element is a thermocouple or thermistor;

a memory device is associated with the recording device enabling the continuous recording of only the outline of the recording curve connecting the recording points corresponding to the minimum recorded temperatures, i.e. instantaneous filterability points.

According to the invention the substance to be analyzed is pumped at a constant flow rate by a volumetric pump in a measuring circuit which is in turn cooled by a cooling bath having a temperature which is maintained at a value sufficiently below the estimated or assumed filterability point; the substance flows through one or more passages of sufficiently small cross-section in the measuring circuit to favor the crystalization of paraffin. Heating means constituted by a heating element are controlled by differential pressure responsive switching means. After the substance passes through this part of the circuit, the change of temperature is monitored from outside the housing by means of a thermosensitive element, the substance thus analyzed at the outlet of the measuring circuit is carried to a recovery circuit. The apparatus is automatic by means of the differential pressure responsive switching means mounted between the delivery end of the volumetric pump and the outlet of the measuring circuit.

Examples of devices for carrying out the method according to the invention for the continuous automatic analysis of the filterability point of Diesel oil in the process of manufacture are described hereinafter with reference to the accompanying drawings in which.

Figure 1:
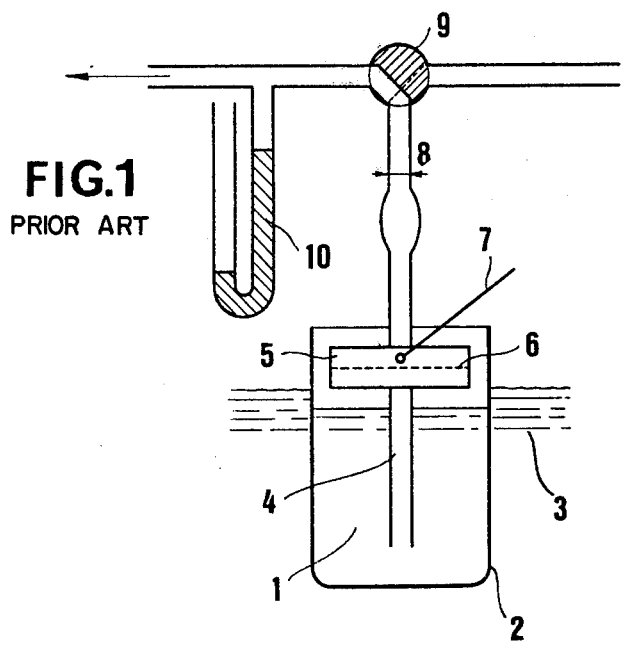
FIG. 1 shows a prior art device.
Figure 2:
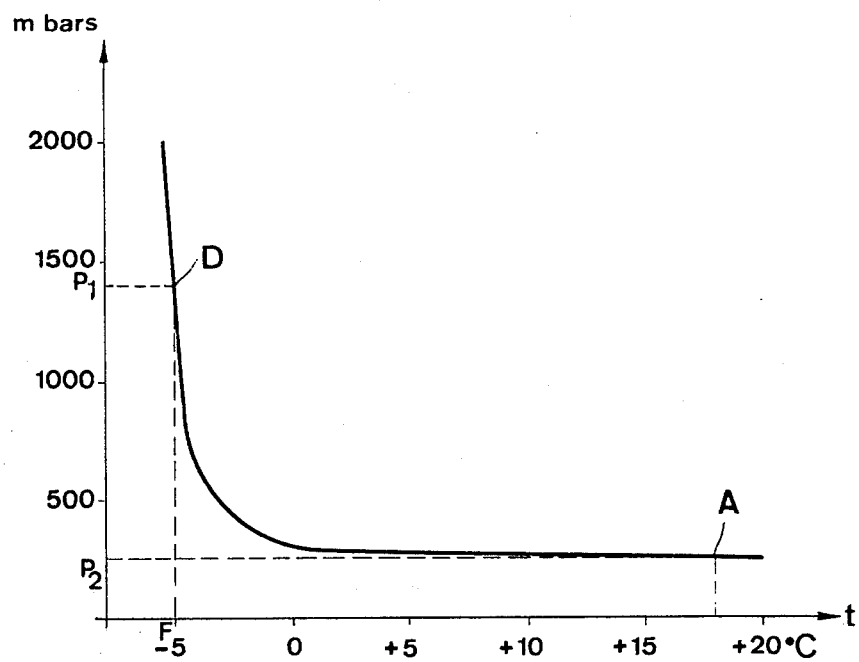
FIG. 2 is a graph showing the temperature pressure drop relationship.

FIG. 2 shows the relationship between the temperature and the pressure drop. Temperature in centigrade degrees is marked along the X-axis and the pressure drop in millibars is marked along the Y-axis. On this graph clearly appears the distinct change of direction of the curve: at elevated temperatures, about 20°C, the pressure drops being slight, then when the temperature drops, the increase in the pressure drop is at first slight as long as the temperature is sufficiently above the filterability point (F) and then rapid as soon as the temperature drops below the filterability point (F) which is in the order of −5°C for the substance to be analyzed in a particular apparatus in operation. The other values marked on the curve of FIG. 2, pressure drop and temperature, were also determined for the particular example given by way of illustration.

In the curve the operating points P corresponding respectively to the values of pressure drop P1 and P2 are indicated on the Y-axis, of the differential pressure responsive means, the function of which will be described hereinbelow. The point D indicates the beginning of reheating, i.e. a pressure drop of about 1400 mbars ($P_1$) and the point A corresponds to end of heating, i.e. a pressure drop of about 250 mbars (P2).

Figure 3:
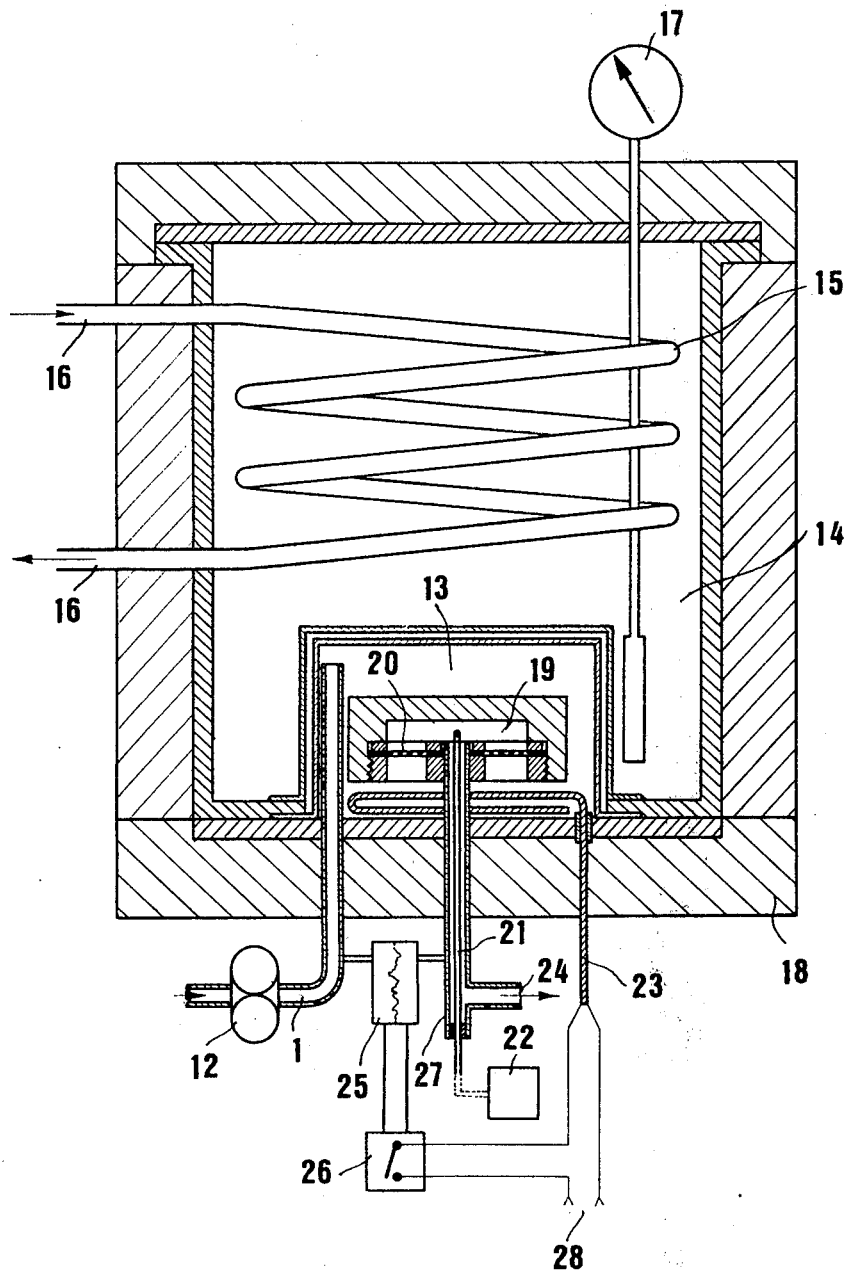
FIG. 3 represents diagrammatically an apparatus according to the invention.

FIG. 3 schematically illustrates an analyzer apparatus.

A small geared volumetric pump 12 arranged at the inlet end of the apparatus is connected to the measuring chamber 13 by a tube. The measuring chamber 13 is housed at the bottom of a heat insulated housing 18 provided to ensure a temperature of about −30°C in the cooling bath 14 filling the housing 18. The insulated housing is provided with a cooling circuit or coil 15 connected to the outside with a small cooling unit having tubes 16. A device 17 for measuring the temperature is immersed in the cooling bath and is readable from outside the housing 18.

The measuring chamber contains a filtering chamber 19 provided with a filter having a standardized mesh 20 and at the outlet or downstream side of the filter, a thermosensitive element 21 which may be a thermocouple or a thermistor. The thermosensitive element 21 is connected to a recording device 22 displaying the changes of the temperature of the substance being filtered.

In the lower portion of the measuring chamber a shrouded Pyrotenax screened heating resistance 23 is positioned, said heating element being rather powerful, about 200 watts, and the mass of substance to be heated is about 80 grams. The end of the heating element or resistance heater 23 outside the housing 18 is electrically connected to two leads, one of the leads being connected directly to a power supply 28 and the other being connected to the switch of the differential pressure responsive means hooked up between the outlet or delivery side of the volumetric pump 12 and the outlet of the measuring chamber, the outlet 27 being connected to a recovery circuit 24.

The dynamic action of the apparatus is described herebelow.

When the apparatus is put into operation, the substance to be analyzed which in Diesel oil in the example, is pumped to the measuring chamber 13 by means of a small geared volumetric pump 12 having a constant flow rate which for the pilot set up was about 2 liters/hour. The Diesel oil is introduced into the measuring chamber 13 at a temperature near to that at which the Diesel oil is produced, the chamber 13 being immersed in a cooling bath 14 which, for example, may be glycolated water. The cooling bath 14 is kept at a temperature in the order of −30°C, the bath being associated with an evaporator circuit 15 operating by means of a small cooling unit. The temperature of the cooling bath is monitored by means of a thermometer 17 from which one can ascertain that said temperature always preserves its desired value whereby the temperature inside the heat insulated housing 18 can be read from outside thereof.

The constant flow rate ensured by the volumetric pump 12 causes a slight pressure drop in the circuit, including the filter 20. The cooling bath 14 cools the Diesel oil circulating in the filter 20 progressively to a temperature close to the filterability point temperature which causes an accumulation of micro-crystals of paraffin in the filter, thereby rapidly increasing the pressure drop across the filter.

For progressively lowering its temperature, the substance to be analyzed flows through a measuring chamber 13 immersed in the cooling bath 14 rather than directly in a cooling tube immersed in the bath; at the outlet of the tube the substance 1 passes into a filtering chamber, the use thereof enabling the concentration of the variations in the filtration pressure drop across the filter itself.

Indeed, in the feature utilizing a tube directly immersed in the bath, a progressive reduction of the effective section of the cooling tube occurs during the temperature lowering sequence. In such a case a spurious pressure drop results, limiting the sensitivity of the apparatus owing to the accumulation of micro-crystals of paraffin all along the inner wall of the cooling tube.

The increase in pressure drop across the filter is detected by the differential pressure responsive switching means 26 having one branch tube connected to the outlet 27 of the filtering chamber 19 and another branch tube connected to the outlet or delivery side of the volumetric pump 12. This increase in pressure drop causes the actuation of the associated switch 25 at a pressure corresponding to point D in FIG. 2, i.e. about 1400 millibars: the value chosen for the pilot during operation.

Through the intermediary of the switch 26 associated with the differential pressure responsive switching means 25, the power supply 28 supplies the resistance heater 23 thereby causing a rise in temperature in the circuit of the measuring chamber 13, including the filtering chamber, thus ensuring the melting of all the micro-crystalls deposited on the filter.

The hysteresis of the differential pressure responsive means 25 is adjusted so that the heating stops as soon as a value ΔP a little greater than the initial is reached, the thermal inertia ensuring the return to the actual initial condition corresponding to point A in FIG. 2, i.e. about 250 millibars.

A second sequence then begins automatically and so on and so forth.

Figure 4:
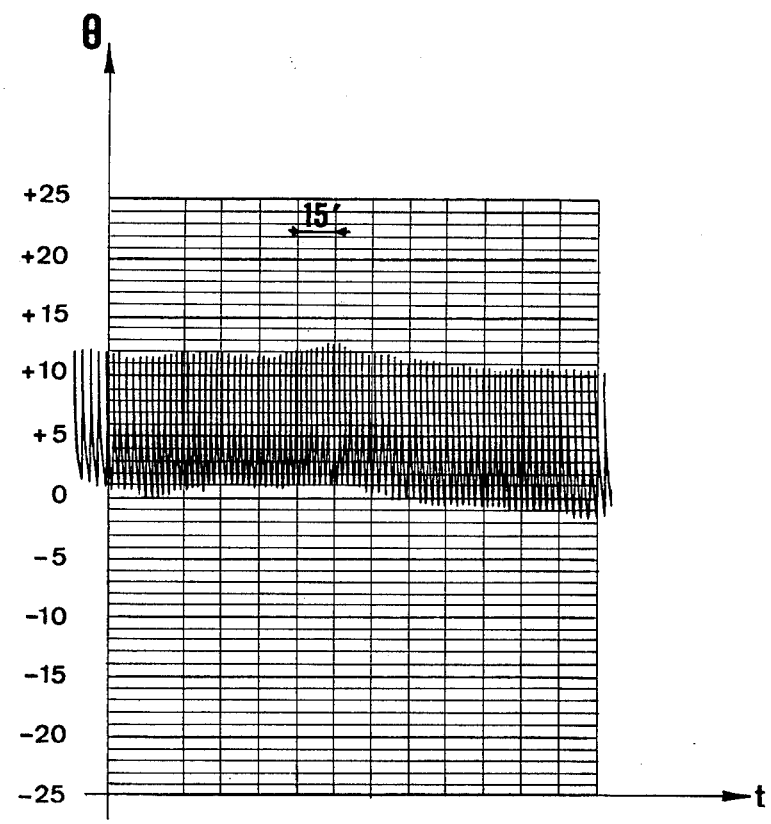
FIG. 4 is the result of the continuous recording of the filterability point temperature.

The temperature of the Diesel oil being filtered measured by means of the thermosensitive element or sensor 21 may be read on a recording device 22, the variations thereof being shown in the graph of FIG. 4. This graph shows the continuous recording of the filterability temperature. The time $t$ is marked along the X-axis and the temperature differential $\theta$ is marked on the Y-axis. Successive sequences of analysis are shown in the form of sawteeth having minima corresponding to the values of the filterability point since this is the temperature at which there is clogging of the filter 20, the resultant increase in pressure drop bringing about the start of the preheating cycle.

It is also possible to associate a memory device with the recording device thereby enabling the continuous recording only the minima of the sawtooth formation.

The measuring apparatus according to the invention may possibly be incorporated in a Diesel oil use and/or processing installation. For example, the arrangement could easily be associated with a device enabling the treatment of Diesel oil in order to improve the value of its filterability point. The recording device 22 could in such a case be connected to a sensor which would automatically actuate the treatment device as soon as the filterability point reaches a predetermined value. A control system is thus obtained by using the measurement data furnished by the apparatus according to the invention.

Figure 5:
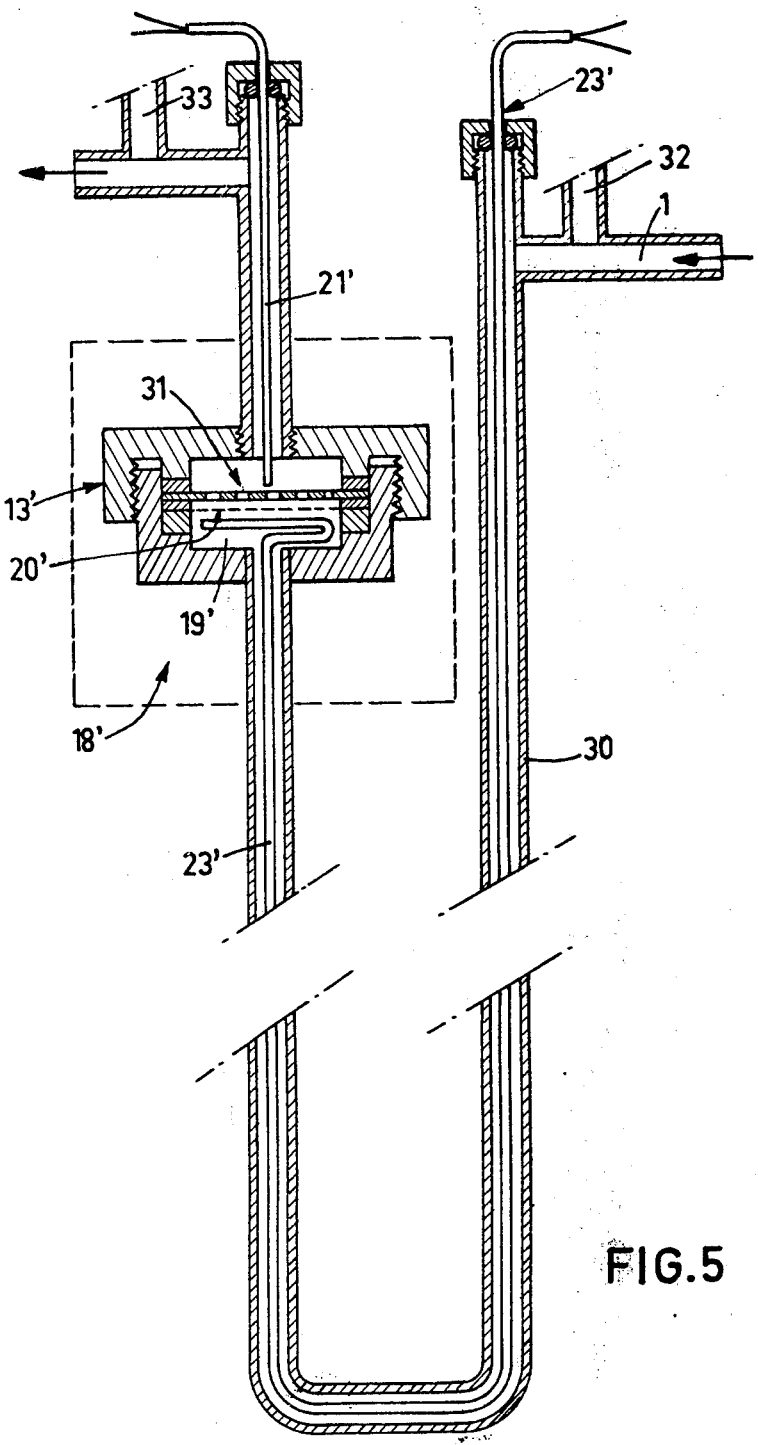
FIG. 5 shows an alternative embodiment of the apparatus.

There now follows a description of an alternative embodiment of the apparatus for the continuous automatic analysis of the filterability point of a liquid substance, particularly Diesel oil in the process of manufacture. In order to facilitate a better description of the device according to the invention, certain details will be specified and various numerical values corresponding to the embodiment of FIG. 5 will be given. This in no way limits the invention to said details and various numerical values, the construction and operation of the device remaining substantially unchange.

The apparatus, for carrying out the method according to the invention comprises at its inlet end means for pumping about 2 liters/hour of Diesel oil 1 to be analyzed, a measuring chamber 13' at the delivery side of the pumping means connected to the inlet end of a mesuring circuit tube 30 having an inner diameter of about 3 mm. A 24 watt Pyrotenax heating element 23' having a 2 mm diameter is mounted in the tube 30 and extends along the entire length thereof as well as into the upstream portion of the measuring chamber 13'. The measuring chamber 13' is arranged in a heat insulating housing 18' containing a cooling bath; the filtering chamber 19' is also arranged in the measuring chamber 13' and includes a circular filter 20' having 19 mm diameter and a 45 $\mu$M mesh. The measuring chamber 13' also includes a divider 31 in the form of a perforate plate, and a thermosensitive element 21' disposed at the downstream side of the filter 20' and the divider 31 along the flow path of the liquid substance. The high pressure side 32 of a differential pressure responsive means connected at the inlet end of the measuring circuit tube 30 and the low pressure side 33 is connected at the outlet end of the measuring chamber 13' after flowing by the thermosensitive element 21' at its low pressure side 33.

The apparatus according to the invention includes a differential pressure responsive means which may have different technical constructions. Nevertheless the technical solution opted for, insofar as the differential pressure actuator is concerned, must offer the possibility of adjusting the operating point of the hysteresis loop; a differential pressure responsive means is described hereinafter which may be employed in carrying out the method according to the invention.

Figure 6:
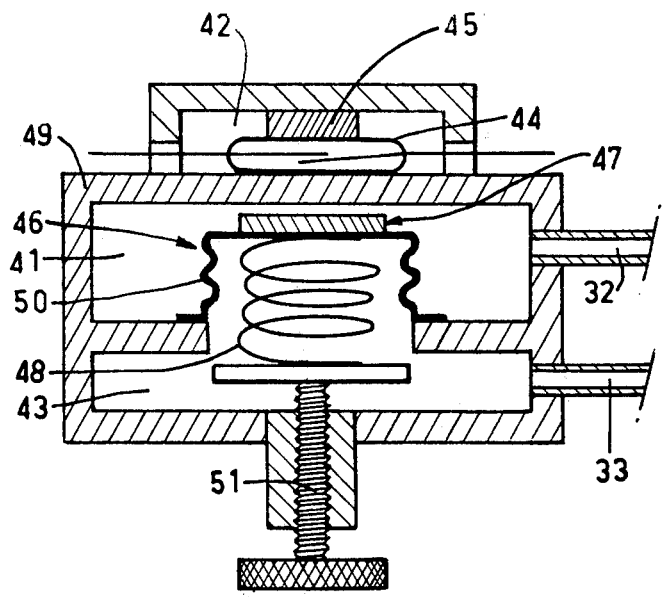
FIG. 6 is a schematic illustration of the differential pressure responsive switching means.

The differential pressure responsive switch illustrated in FIG. 6 includes three chambers 41, 42, 43; the inlet chamber 41 is joined to the high pressure connection 32. Chamber 41 is moreover in magnetic association with the switch chamber 42 by virtue of a magnet provided in each of these two chambers. The closed switch chamber 42 which is in adjacent superposition with respect to the chamber 41 houses both a magnetically responsive switch 44 connected to the power supply for the heating element 23 and a polarizing magnet 45. The chamber 41 includes sealed central cylindrical zone 46 which is defined by a bellows member 50 which supports on its top surface an actuator magnet 47 facing the adjacent wall 49 common to chambers 41 and 42. The inner side of the sealed cylindrical zone 46 is in communication with the outlet chamber 43; a coil spring 48 is provided in the sealed cylindrical zone between the underside of the top surface of the bellows 50 and an adjustment screw 51 with its knurled knob accessible to the outside. The outlet chamber 43 is connected to the high pressure connection 33.

The operation of the differential pressure switch will now be described.

As described above, the constant flow rate at the inlet of the overall apparatus causes a slight pressure drop in the measuring circuit; the progressive fall in the temperature due to the cooling system brings the Diesel oil flowing in the filter 20' to a temperature close to the filterability point and causes the accumulation of micro-crystals of paraffin on the filter and the rapid increase in the pressure drop across the filter. This increase in the pressure drop actuates the differential pressure responsive switch means at a pressure corresponding to point D in the graph of FIG. 2.

Indeed, when there is an increase in the pressure drop, the pressure differential between the chambers 41 and 43 decreases which causes an expansion of the bellows 50 so that the actuator magnet 47 on the top surface of the bellows comes closer to the common wall 49 separating the chambers 41 and 42. The actuator magnet 47 of polarity opposite that of the magnet 45 is pulled farther towards the common wall thereby opening the switch magnetically, the switch being normally closed. The heating element is then supplied through a reversing relay not shown, the temperature in the measuring circuit 13 then increases by the heating element thereby melting all the micro-crystals of paraffin previously deposited on the filter. The reheating causes the pressure drop across the filter to decrease, the pressure in the chamber 41 thus increases with respect to the chamber 43, and the bellows 50 contracts carrying with it the actuator magnet 47 away from the common wall 49 and the other magnet 45. The differential pressure switch is adjusted by means of the adjustment screw 51 effectively controlling the position of the actuator magnet 47 with respect to the common wall 49 of the chambers 41 and 42. This adjustment is made so that as soon as the value of $\Delta P$ is a little greater than the initial value, the distance between the two magnets 47, 45 corresponds to the point at which the magnet 45 causes the switch 44 to open. The power supply to the heating element 23 is thus cut off.

A second sequence or cycle thus begins automatically and so on.

A preferred embodiment of the device according to the invention will now be described with reference to FIGS. 7 and 8.

Figure 7:
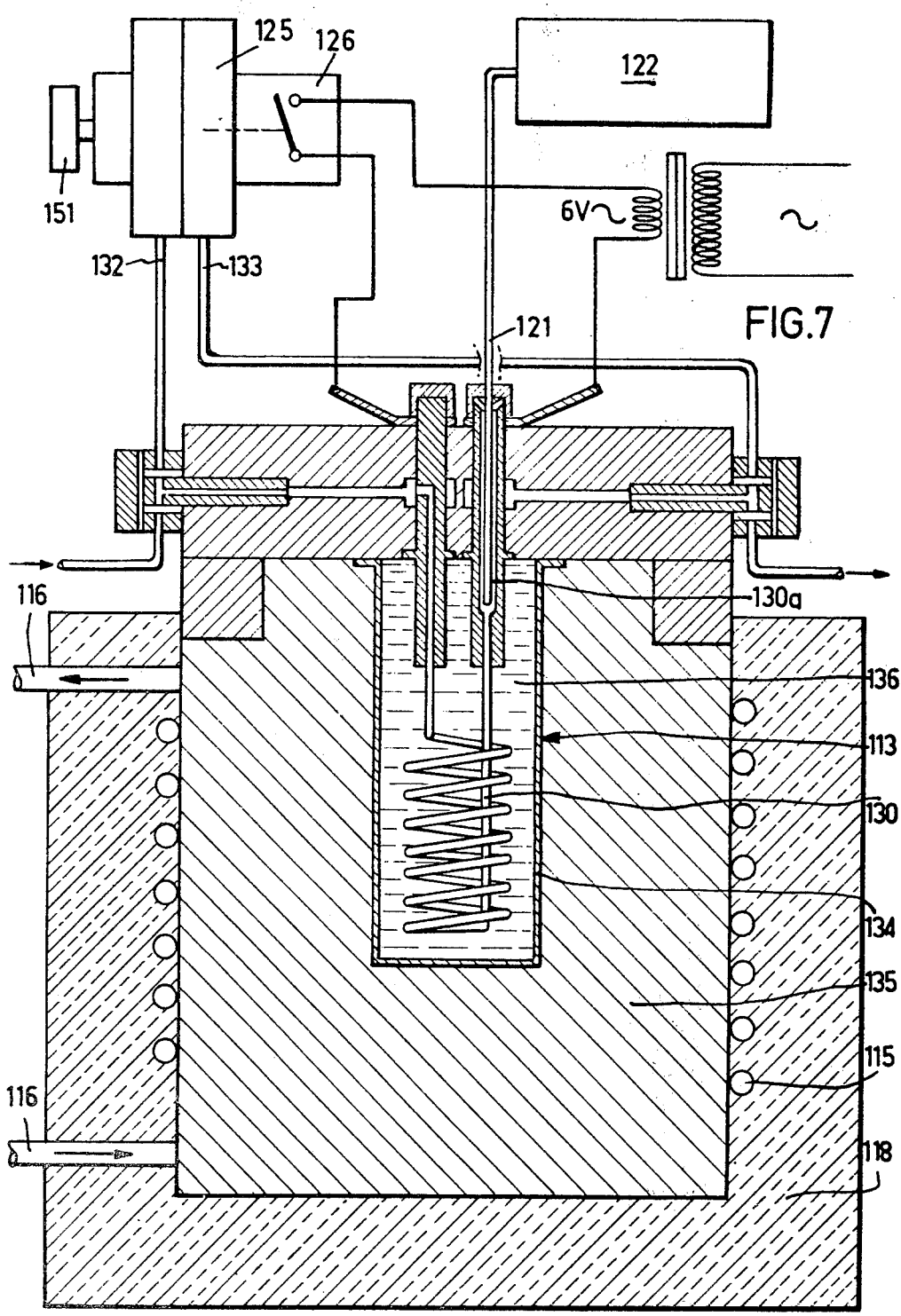
FIG. 7 is a schematic illustration of the apparatus according to a preferred embodiment.

The filterability point analyzer apparatus shown in FIG. 7 comprises a measuring circuit including a stainless steel capillary tube 130.

The substancce to be analyzed flows through the capillary tube 130 which passes through a measuring well 113 which is constituted by a limited capacity cavity of about 80 cm$^3$ formed in a solid mass 135 of steel. The capillary tube has an outer diameter of 1.5 mm and an inner diameter of 1.2 mm and is formed so as to provide a rather substantial surface area in the measuring well; the tube 130 may, for example, be of helical configuration as illustrated in FIG. 7.

The measuring well 113 is lined with a Teflon sleeve 134 and filled with a non-freezing liquid 136.

The solid mass 135 of steel is cylindrical and is provided with a tubular evaporator 11, for a cooling unit connected at 116 and coiled thereabout.

The capillary tube is about 100 cm long and has an electrical resistance of about 1 ohm. The inlet and outlet ends of the tube are mounted in bushings formed of insulating material and are connected across a switch 126 of a differential pressure responsive switching means 125 to a 6 true volt potential difference. The capillary tube thus constitutes a heating element which consumes about 36 watts.

The capillary tube 130 has a widened portion 130a at the outlet of the measuring well, in order to receive a thermosensitive element 121 therein. The free end of the thermosensitive element 121 may be connected to a temperature recording device 122 and the bushing between the poritons of the element 121 located inside or outside the measuring circuit hermetically seals the tube 130.

The capillary tube 130 extends perpendicular to the widened portion 130a before communicating with the surambient atmosphere.

This embodiment of the filterability point analyzer apparatus is preferred over the other embodiments previously described because it is of simplified construction and its design enables improved results.

The operation of the last-described analyzer is substantially the same as the other described embodiments; the specific aspects will be emphasized in the following description.

A constant flow rate of the substance to be analyzed is provided at the inlet which enables the continuous circulation of the substance in the capillary tube 130. The continuous circulation in the analyzer apparatus causes a pressure drop in the circuit, then the progressive lowering of the temperature due to the cooling unit brings the substance circulating in the measuring circuit 130 to a temperature close to the value corresponding to the filterability point and causes the accumulation of micro-crystals of paraffin along the inner wall of the capillary tube 130 and the rapid increase of the pressure drop in the measuring circuit 130.

An increase in the pressure drop to about 1400 millibars brings about the actuation of the differential pressure responsive means 125, i.e. the differential pressure responsive switch connected to the capillary tube 130 controls the starting of the reheating sequence by applying a potential difference of 6 true volts to the terminals of the capillary tube 130. The capillary tube has a resistance of 1 ohm; the heating element constituted by the tube consumes 36 watts. The metal wall of the capillary tube heats up and enables the efficient melting of the micro-crystals which were deposited thereon.

The pressure drop due to the reduction of the effective cross-section caused by the crystallization of paraffin along the inner wall thereof, for a constant flow rate, rapidly returns to the initial value and in the proximity thereof, viz near 700 millibars, the differential pressure switch 125 brings the heating sequence to an end, thereby enabling a new cooling sequence to begin.

The cooling is effected by means of the cooling bath 136 which is adapted to remove calories from the substance to be analyzed while providing a moment of thermal inertia sufficiently large so as to eliminate the inevitable variations in temperature resulting from the one and off operation of the cooling unit.

The elimination of variations is brought about by means of the solid mass 135 of steel. The specific heat of the steel is about one-eighth the specific heat of an aqueous solution but its density which is about seven times greater gives for an equivalent volume a moment of thermal inertia substantially equal to that of the liquid bath 14 in the previously described embodiment.

The measuring well 113 is filled with a non-freezing liquid 136 with a view to ensuring that heat transfer between the low temperature source which is constituted by the metal mass 135 and the capillary tube 130 immersed in the measuring well.

The temperature of the non freezing liquid is intermediary regulated in the course of the sequence by the periodic reheating of the capillary tube while the temperature of the solid mass 135 is maintained at a constant temperature of −25°C by the thermostat of the cooling unit.

Figure 8:
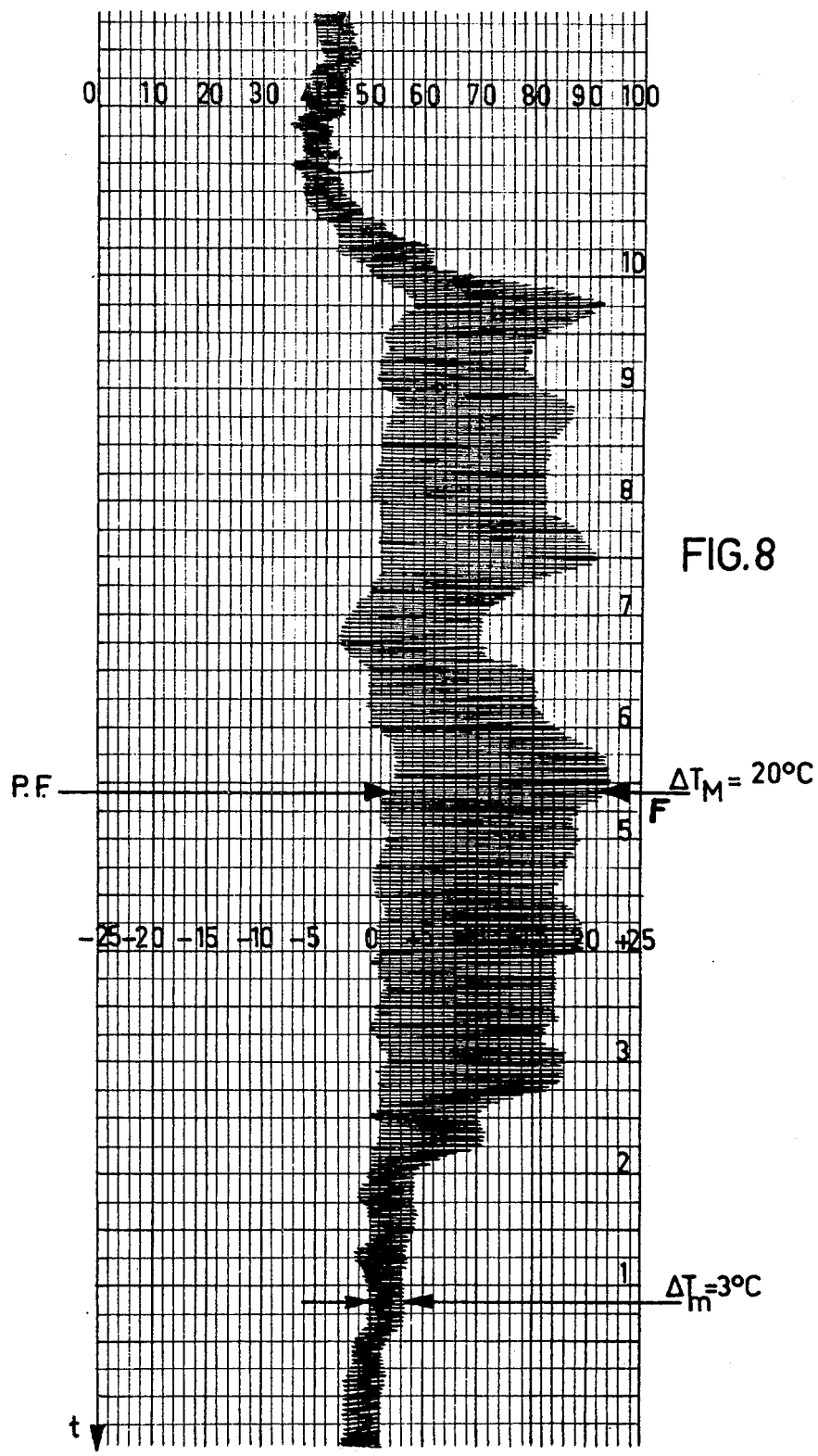
FIG. 8 shows the results of a continuous recording of the filterability point temperature using the apparatus shown in FIG. 7.

The thermocouple 121 which measures the filterability point temperature remains at the outlet end of the capillary tube 130 and enables the continuous recording of the changes of the temperature between the minima representing the variations of the filterability point P.F. and the maxima representing the maximum temperature reached for ensuring the complete melting F of the micro-crystals (FIG. 8).

This preferred analyzer apparatus demonstrates further advantageous characteristic. Indeed, for the preadjusted range of $\Delta P$ at the terminals of the capillary tube, about 700 millibars, the recorded temperature varies substantially between a minimum value $\Delta Tm$ of 2° to 3°C and a maximum value $\Delta T_M$ which may reach 15° to 20°C for the same filterability point. Now, since the maximum temperature attained for ensuring the melting of all the micro-crystals and the return to the initial $\Delta P$ is variable according to the distillation cross-section representing the substance to be analyzed, the continuous recording of the temperature of the substance leaving the capillary tube allows not only the instantaneous value of the filterability point to be determined but also the quality of the cracking or fractional distillation in the cracking or distillation tower.

If the molecular weight of the crystallizable paraffins is relatively grouped, the difference between the melting points of the lightest and heaviest remains slight, thereby proving a good fractional distillation. On the other hand, if the distillation tower operates improperly or if there is a breakdown, the molecular weight and melting temperature of the crystallizable paraffins are more scattered which is transcribed by the recording device as a rise in $\Delta T$.

This phenomenon may be taken advantage of for using the data from the analyzer by transmitting it to the control system for the distillation tower in order to vary the parameters accordingly and thereby obtain a kind of self-regulation or feedback control.

What we claim is:

1. An apparatus for the continuous automatic measure of the filterability threshold temperature of a liquid substance comprising a block made of a metal having a high thermal inertia, said block having an external surface and a closed recess therein, a cooling liquid substantially filling said recess, said cooling liquid having a freezing temperature substantially lower than the average filterability threshold temperature of the type of liquid to be analyzed, cooling means on said external surface of said block adapted to cool said block, an electrically conductive metal capillary tube immersed in said cooling liquid and having an inlet end and an outlet end emerging from said block, said tube being electrically insulated from said block, pump means for delivering the liquid to be analyzed to said tube at a constant volume flow rate, electrical connecting means to connect both ends of said tube with the terminals of an electric power supply respectively, switch means interposed on one of said electrical connecting means, pressure responsive meeans in connection with said switch means whereby said electric power is supplied to said electrically conductive metal capillary tube when the difference between the inlet pressure and outlet pressure of said capillary tube exceeds a first predetermined value and suspends said supply of electric power when said pressure difference reaches a second predetermined value lower than said first value, thermosensitive means adapted to measure the temperature of the liquid to be analyzed in the outlet end of said capillary tube and means for recording the temperature measured by said thermosensitive means.

2. An apparatus according to claim 1, wherein the thermosensitive element is a thermocouple.

3. An apparatus according to claim 1, wherein the thermosensitive element is a thermistor.

4. An apparatus according to claim 1, further comprising a memory device associated with said recording means enabling the continuous recording of only the outline of the recording curve connecting the points corresponding to the minimum temperatures recorded, i.e. instantaneous filterability points.

* * * * *